Sept. 9, 1952 T. B. STRIBLING, JR Plant Pat. 1,127
PEACH TREE
Filed Sept. 22, 1951
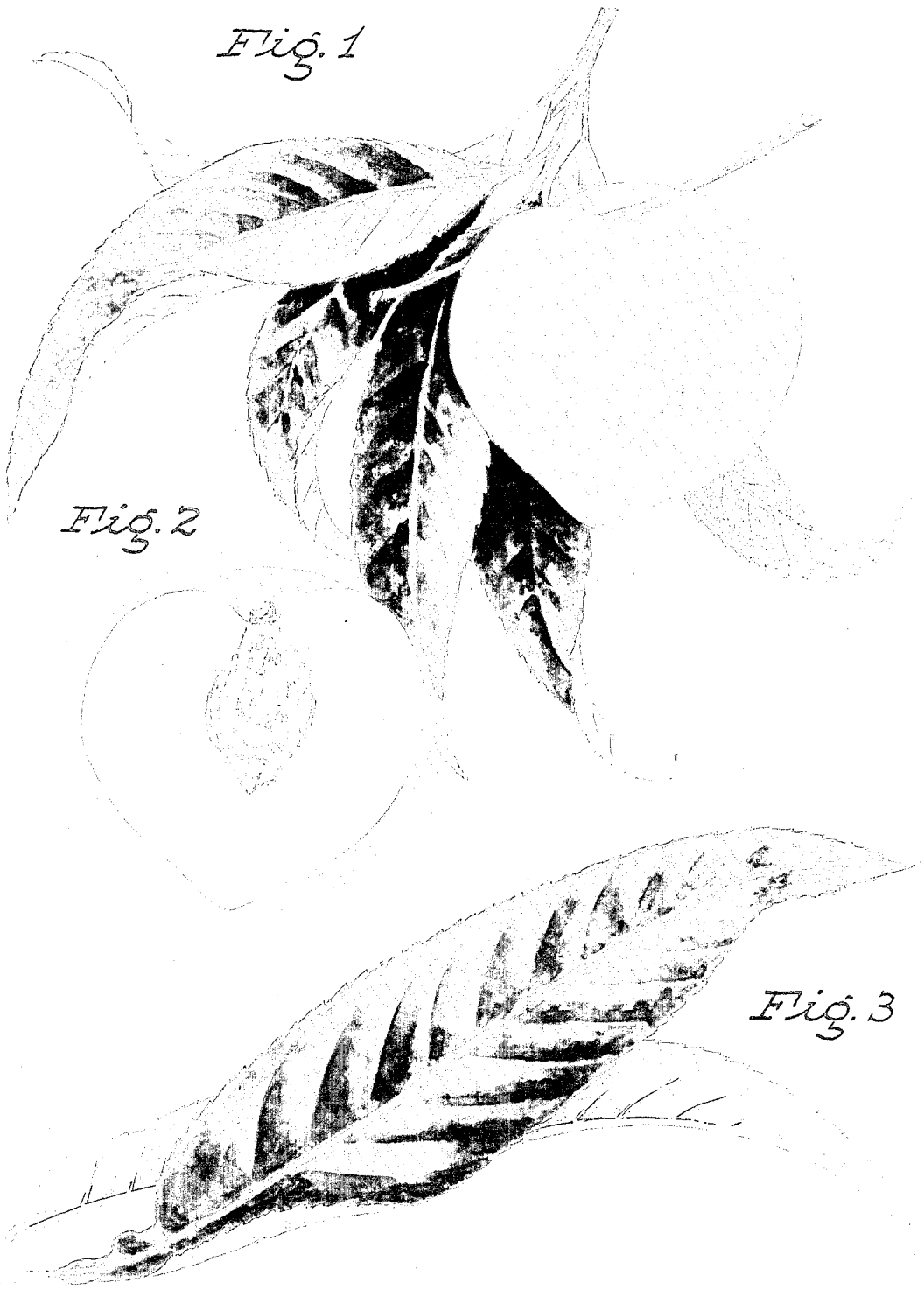
WITNESS
Addison E Avery
INVENTOR
Thos. B. Stribling Jr.
Webster & Webster
ATTYS.

Patented Sept. 9, 1952

Plant Pat. 1,127

UNITED STATES PATENT OFFICE 1,127

PEACH TREE

Thomas B. Stribling, Jr., Merced, Calif.

Application September 22, 1951, Serial No. 247,817

1 Claim. (Cl. 47—62)

This invention is directed to a new and distinct variety of peach tree which bears yellow-fleshed freestone fruit having characteristics which make it desirable in the early market for table or dessert use.

The primary novel feature of this variety is the early ripening period of the fruit, coupled with the fact that its yellow-fleshed freestone fruit is good size, well shaped, and highly colored; the latter being very exceptional in an early ripening peach.

Another valuable feature of the instant variety is that the fruit is sufficiently firm to be a good early shipper.

Additional advantageous features of the variety are that the tree is a vigorous grower and consistent bearer, and that a good set of fruit is produced even in a mild winter; this latter feature distinguishing from many other early peaches which require a freezing winter for good setting of the crop.

The new and distinct variety of peach tree herein described was originated and successfully asexually propagated in the following manner:

A substantial number of the seeds of the July Elberta variety were planted in January of 1945 in applicant's growing plot near Le Grand, Merced County, California.

In June of 1945 the resulting seedlings, then very small, were cut and budded onto year-old root stock trees; such top-worked root stock trees having borne several fruit in the harvest season of 1946. Such initial fruit, along with that borne by the trees in the harvest season of 1947, was given close and careful observation in both years, and the present variety—because it evidenced very substantial promise by reason of certain new and distinctive pomological characteristics thereof, as will hereinafter appear—was selected for the purpose of further observation, and propagation.

In 1947 this variety of peach tree was top-worked, at the aforesaid growing plot, onto a young experimental orchard, which fruited first in 1949; such fruit, and the fruit of the subsequent harvest seasons of 1950 and 1951 from said orchard, having been the subject of careful comparisons with the fruit of the parent tree. As a result of such comparisons it has been definitely ascertained that the asexual reproductions of the variety carry forward each and every one of the novel features of said parent tree and its fruit.

In the drawings:

Fig. 1 is a perspective view of the fruit of the new variety, together with stems and leaves.

Fig. 2 is a sectional view of one of the fruits, with the stone exposed.

Fig. 3 is a perspective view showing a pair of leaves; one leaf showing the top side, and the other leaf showing the under side.

Referring now more specifically to the pomological details of this new and distinct variety of peach tree, the following is an outline description thereof; all major color plate identifications being by reference to Maerz and Paul Dictionary of Color.

Tree: Large; vigorous; upright; dense; hardy; very productive; regular bearer.

Trunk: Medium size; medium texture.

Branches: Medium size; medium texture; brown with green.

*Lenticels.*—Medium number; medium size.

Leaves: Medium size, averaging 7″ in length and 1½″ in width; acuminate; lanceolate; acutely pointed; medium thick; smooth. Color—Medium green (23–L–6) on top side; lighter green (21–J–4) tending to yellowish on the under side.

*Margin.*—Crenate; finely serrate.

*Petiole.*—Medium length, ½″ average; medium thickness.

*Glands.*—Average number, six; alternate; medium size; reniform; green; on petiole and blade.

*Stipules.*—Lacking.

Flower buds: Half hardy; medium size; medium length; conic; flowers are self-fertile.

Flowers: Average date first bloom, March 7th; average date full bloom, March 14th. Normal—local (with July Elberta). Medium blooming period compared with other varieties. Medium, size. Color—pink. Anthers—red.

Fruit:

*Size.*—Somewhat variable; large to medium, averaging 2⅛″ in axial diameter and 2½″ transversely in the suture plane.

*Form.*—Uniform; symmetrical; globose.

*Suture.*—An inconspicuous line; shallow, extending from base but discontinues at apex, with slight depression beyond pistil point.

*Ventral surface.*—Rounded slightly, lipped toward base on both sides; lips equal.

*Cavity.*—Flaring. Elongated in the suture plane, with suture showing on both sides. Average depth—½″. Average breadth—¼″.

*Base.*—Rounded.

*Apex.*—Short to prolonged, pistil point apical.

Skin: Medium thickness; tender; free; slight tendency to crack.

*Color.*—Yellow background almost completely overspread with maroon red, with no definite contrast between the sides, shading from lighter (5–A–12) to darker (5–L–10); there being relatively darker mottling or streaking on the fruit, as shown.

*Down.*—Moderate to scant; short; does not roll up when rubbed.

Flesh:

*Color.*—Yellow (9–L–6) with a few reddish streaks (1–K–11) adjacent the stone near the apex.

*Surface of pit cavity.*—Pale pink with pink fibers.

*Amagydalin.*—Moderate.

*Juice.*—Abundant; rich.

*Texture.*—Firm to medium; crisp; melting.

*Fibers.*—Few; fine; tender.

*Ripens.*—Evenly.

*Flavor.*—Acid; mild; delicate.

*Eating quality.*—Good to best.

Stone: Free.

*Fibers.*—Short; parts from flesh when fully ripe; retains short fiber-like threads along ridges.

*Size.*—Small. Average length, 1¼″; average breadth, 1″; average thickness, ¾″.

*Form.*—Obovoid; crenate toward base.

*Base.*—Straight.

*Hilum.*—Narrow; oblong.

*Apex.*—Acute.

*Sides.*—Equal.

*Surface.*—Regularly furrowed throughout. Ridged toward apex; pitted toward base.

*Ridges.*—Rounded.

*Pits.*—Elongated.

*Ventral edge.*—Thin with wing throughout.

*Dorsal edge.*—Full with shallow narrow groove throughout.

*Ridges.*—On either side; continuous.

*Color.*—Light brown (14–B–8) shading to 14–A–11.

*Tendency to split.*—Slight.

Use: Early market; local; dessert; shipping.

Keeping quality: Good to medium.

Shipping quality: Good to medium.

As compared to other varieties of peach trees the instant variety ripens between the Mayflower and Alexander, and at the same time as the Florence peach; the latter being one of the early bearing standard peach trees in Western fruit commerce. However, as the Florence peach tree bears fruit which is white-fleshed, the yellow-fleshed fruit of the present variety is a distinct advantage, as the trade prefers the latter.

Other advantages of the fruit of the present variety over the Florence peach are larger size of the fruit; more colorful skin on the fruit; and greater resistance of the tree to disease.

As compared to the yellow-fleshed Red Haven freestone peach the present variety has the distinct advantage of ripening and being available to the market eighteen days earlier, in addition to being rounder and having a more spherical form.

In comparison to the parent July Elberta peach the present variety has inherited the vigorous growing habit and consistent bearing qualities thereof; carrying forward the freestone characteristic and being completely free when ripe enough for eating.

Distinguishing from the Elberta the present variety is rounder, of more spherical shape, and more important it ripens on the average thirty-five days earlier.

To applicant's knowledge the peach varieties Mayflower, Alexander, Florence and Red Haven are unpatented; July Elberta being the subject of U. S. Plant Patent 15.

Of common parentage with the variety of peach shown in copending application for United States Plant Patent, Serial No. 190,505, the present variety is distinct in that it ripens three to five days earlier; is more colorful, being shaded reddish maroon over-all, with dark maroon streaks or blotches, with a minimum of yellow showing through, and with not as much contrast between the sunny side and the shady side of the fruit. Other distinguishing characteristics between the variety of peach shown in such copending application and the present variety are that the fruit of the latter is more tart or acid, and such fruit, while having scant fuzz or down on the skin, has more than said first named variety.

The tree and its fruit herein described may vary in slight detail due to climatic and soil conditions under which the variety may be grown.

Having thus described my invention, I claim:

A new and distinct variety of peach tree substantially as described and illustrated bearing yellow fleshed, freestone fruit which ripens with the Florence between the Mayflower and the Alexander, the fruit ripening approximately eighteen days earlier than the Red Haven and approximately thirty-five days earlier than the July Elberta, being yellow in under-color almost wholly overspread with reddish maroon with dark mottling thereon, being rounder and of more spherical shape than the Red Haven and July Elberta, having a relatively small pit, and acid flavor; and the tree being a vigorous grower, a consistent bearer, and setting a good crop in mild winters.

THOMAS B. STRIBLING, Jr.

No references cited.